United States Patent
Dellamano et al.

(10) Patent No.: US 10,905,512 B2
(45) Date of Patent: Feb. 2, 2021

(54) GLOVE REMOVER APPARATUS

(71) Applicants: Anthony Dellamano, Mokena, IL (US); Nathan David Cork, Joliet, IL (US); Drew William Johnson, Lincolnshire, IL (US)

(72) Inventors: Anthony Dellamano, Mokena, IL (US); Nathan David Cork, Joliet, IL (US); Drew William Johnson, Lincolnshire, IL (US)

(73) Assignee: MEDHOOK IP, LLC, Joliet, IL (US)

(*) Notice: Subject to any disclaimer, the term of this patent is extended or adjusted under 35 U.S.C. 154(b) by 0 days.

(21) Appl. No.: 16/365,708

(22) Filed: Mar. 27, 2019

(65) Prior Publication Data
US 2019/0298468 A1 Oct. 3, 2019

Related U.S. Application Data

(60) Provisional application No. 62/651,611, filed on Apr. 2, 2018.

(51) Int. Cl.
*A61B 42/50* (2016.01)
*A47G 25/90* (2006.01)

(52) U.S. Cl.
CPC .......... *A61B 42/50* (2016.02); *A47G 25/904* (2013.01)

(58) Field of Classification Search
CPC .... A61B 42/50; A47G 25/904; A47G 25/908; A47G 25/92
USPC .................................. 223/111–112
See application file for complete search history.

(56) References Cited

U.S. PATENT DOCUMENTS

| | | | | |
|---|---|---|---|---|
| 1,059,020 A | * | 4/1913 | Arason | A47G 25/92 24/40 |
| 1,121,521 A | * | 12/1914 | McElroy | A47G 25/905 223/111 |
| 1,215,283 A | * | 2/1917 | Kirkland | A45F 5/02 24/3.6 |
| 5,687,889 A | * | 11/1997 | Liden | A47G 25/80 223/111 |
| 6,176,378 B1 | * | 1/2001 | Neubauer | A47G 25/00 211/113 |
| 6,279,792 B1 | * | 8/2001 | Neal | A47G 25/904 223/111 |
| 8,764,081 B1 | * | 7/2014 | Krieger | A44B 19/262 24/429 |
| 2009/0032423 A1 | * | 2/2009 | Japuntich | A61B 50/362 206/366 |
| 2010/0006609 A1 | * | 1/2010 | McAllister | A47G 25/905 223/111 |

FOREIGN PATENT DOCUMENTS

JP 2015-193975 * 11/2015 ........... A41D 19/015

* cited by examiner

*Primary Examiner* — Nathan E Durham
(74) *Attorney, Agent, or Firm* — Justin Lampel

(57) ABSTRACT

A glove remover apparatus is provided. The glove remover apparatus is especially suitable for the removing of a used medical glove in a sterile manner; however the glove remover apparatus is not limited to removing only medical gloves. The glove remover apparatus may have an extended long handle having a trigger spring at the distal end wherein the trigger spring grasps a glove on the user's hand. Once grasped by the apparatus, the used glove may be safely removed without a user needing to actually touch the glove.

6 Claims, 5 Drawing Sheets

GLOVE REMOVER APPARATUS

REFERENCE TO RELATED APPLICATIONS

This application claims priority to U.S. Provisional Application No. 62/651,611 which was filed on Apr. 2, 2018, the entire contents of which are incorporated by reference herein.

BACKGROUND OF THE INVENTION

A glove remover apparatus is provided. The glove remover apparatus is especially suitable for the removing of a used medical glove in a sterile manner; however the glove remover apparatus is not limited to removing only medical gloves. The glove remover apparatus may have an extended long handle having a trigger spring at the distal end wherein the trigger spring grasps a glove on the user's hand. Once grasped by the apparatus, the used glove may be safely removed without a user needing to actually touch the glove.

Over the years, patents have been issued related to medical gloves. For example, U.S. Pat. Nos. 9,113,666 and 9,445,636 both to George disclose a glove sized and shaped to enclose a human hand, the medical glove having a two-layer cuff, the two layers being fixed to one another at a plurality of locations to define a plurality of spaced apart openings in the cuff, the openings accessible only outside the glove.

Further, U.S. Pat. No. 8,015,622 to Bhalla discloses a sterile glove having a hand and finger portion, a cuff having an inside surface and an outside surface, and a cuff rim. The cuff is adapted to be folded over at a fold when the glove is packaged, and a portion of the inside surface of the cuff becomes an outer facing surface when it is folded over. The glove further includes a detachable tab that is coupled to the inside surface and includes a free end and a non-free end. The glove further includes a detachable shield covering at least a portion of the outer facing surface when the cuff is folded over at the fold.

Still further, U.S. Pat. No. 7,665,150 to Holley discloses a disposable elastomeric glove having a secondary cuff disposed distally of a primary cuff on a wrist region of the glove. The secondary cuff may be grasped by an opposite hand to safely remove the glove with the primary cuff in place to protect the skin on the wrist from contaminants on the opposite hand. The secondary cuff approximates the design of the primary cuff such that the removal process is similar to that of a conventional glove.

However, these patents fail to describe a glove remover apparatus which is easy to use and efficient as is described in the present application. A need, therefore, exists for an improved glove remover apparatus.

SUMMARY OF THE INVENTION

A glove remover apparatus is provided. The glove remover apparatus is especially suitable for the removing of a used medical glove in a sterile manner; however the glove remover apparatus is not limited to removing only medical gloves. The glove remover apparatus may have an extended long handle having a trigger spring at the distal end wherein the trigger spring grasps a glove on the user's hand. Once grasped by the apparatus, the used glove may be safely removed without a user needing to actually touch the glove.

An advantage of the present glove remover apparatus is that the present glove remover apparatus is easy to use.

And an advantage of the present glove remover apparatus is that the present glove remover apparatus reduces or eliminates potential contamination of pathogens in an operating room.

Yet another advantage of the present glove remover apparatus is that the present glove remover has a plurality of grooves for grasping the handle in one embodiment.

Another advantage of the present glove remover apparatus is that the present glove remover apparatus has smooth rounded spherical balls at the end of the device to ensure comfort and to prevent injury when the device slides across the skin of a person to remove the glove in one embodiment.

And another advantage of the present glove remover apparatus is that the present glove remover apparatus is disposable.

Still another advantage of the present glove remover apparatus is that the present glove remover apparatus allows a user to use one hand to remove the glove from the opposing hand.

Yet another advantage of the present glove remover apparatus is that the present device locks the glove to the apparatus wherein the glove cannot be detached from the disposable device.

For a more complete understanding of the above listed features and advantages of the present glove remover apparatus reference should be made to the detailed description and the detailed drawings. Further, additional features and advantages of the invention are described in, and will be apparent from, the detailed description of the preferred embodiments.

DETAILED DESCRIPTION OF THE PREFERRED EMBODIMENTS

A glove remover apparatus is provided. The glove remover apparatus is especially suitable for the removing of a used medical glove in a sterile manner; however the glove remover apparatus is not limited to removing only medical gloves. The glove remover apparatus may have an extended long handle having a trigger spring at the distal end wherein the trigger spring grasps a glove on the user's hand. Once grasped by the apparatus, the used glove may be safely removed without a user needing to actually touch the glove.

Figure 1:
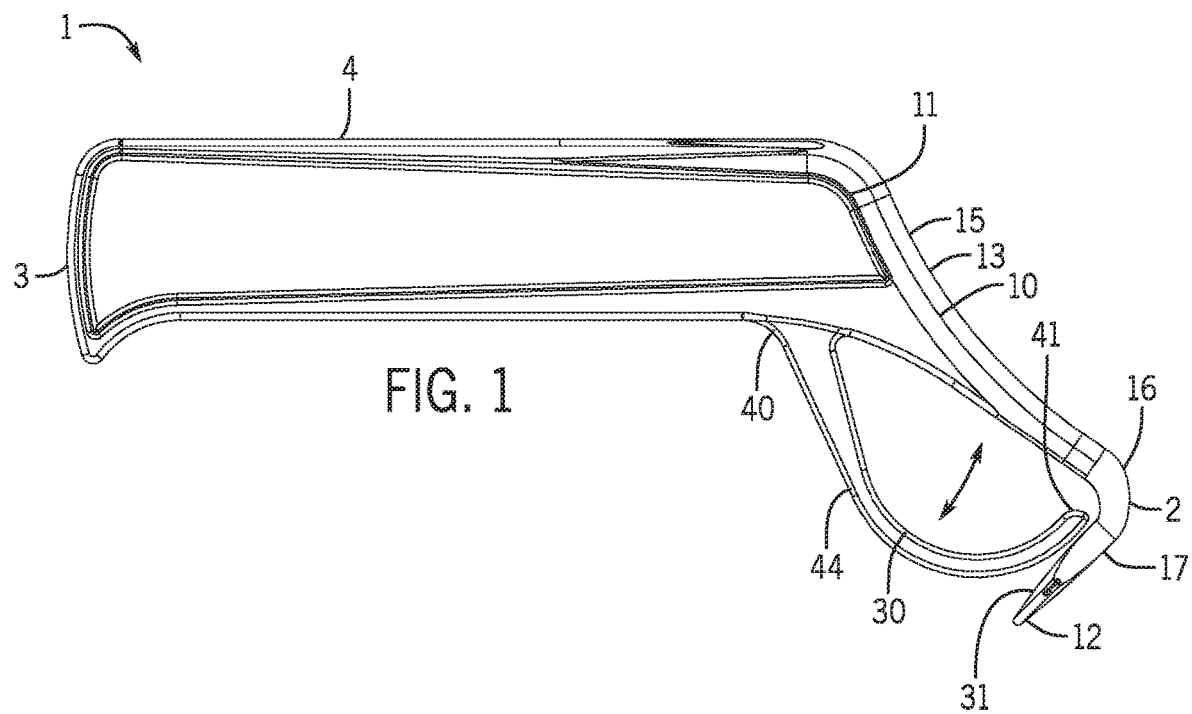
FIG. 1 illustrates a side view of the glove remover apparatus in one embodiment.
Figure 5:
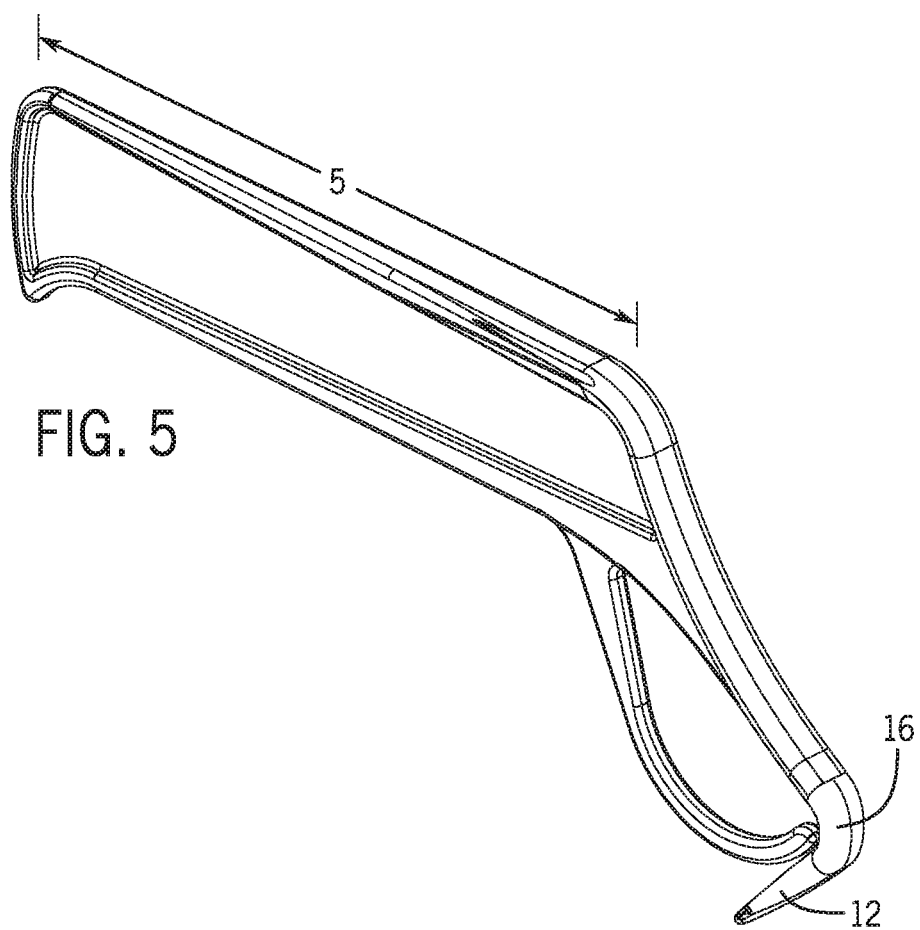
FIG. 5 illustrates a perspective view of the glove remover apparatus in one embodiment.

Referring first to FIG. 1, in an embodiment, a glove remover apparatus 1 is provided. The glove remover apparatus 1 may have a first end 2, a second end 3 and a shaft 4 having a length 5 (FIG. 5). In one embodiment, the shaft 4 is generally flat for easy grasping. Further, in an embodiment, the length 5 of the shaft 4 is roughly the length of a hand so that the shaft 4 may be easily controlled by a hand. Preferably, the apparatus 1 is made of, for example, a durable plastic. In an embodiment, the glove remover apparatus 1 is infused with an antibacterial agent to further prevent the spread of pathogens.

Figure 2:
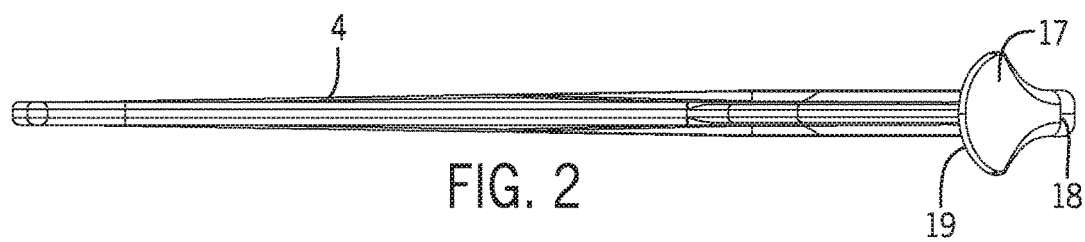
FIG. 2 illustrates a top view of a plurality of glove remover apparatus in one embodiment.
Figure 3:
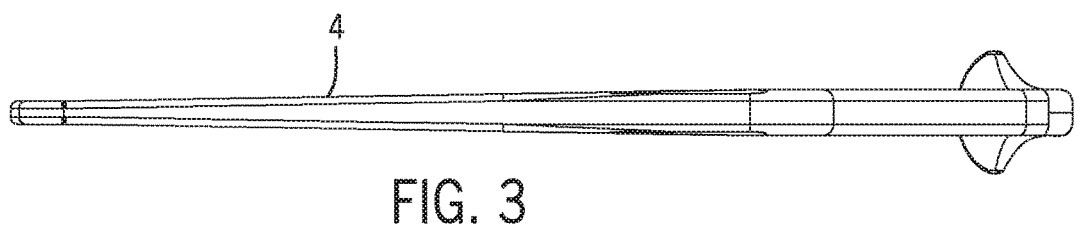
FIG. 3 illustrates bottom view of the glove remover apparatus in one embodiment.
Figure 6:
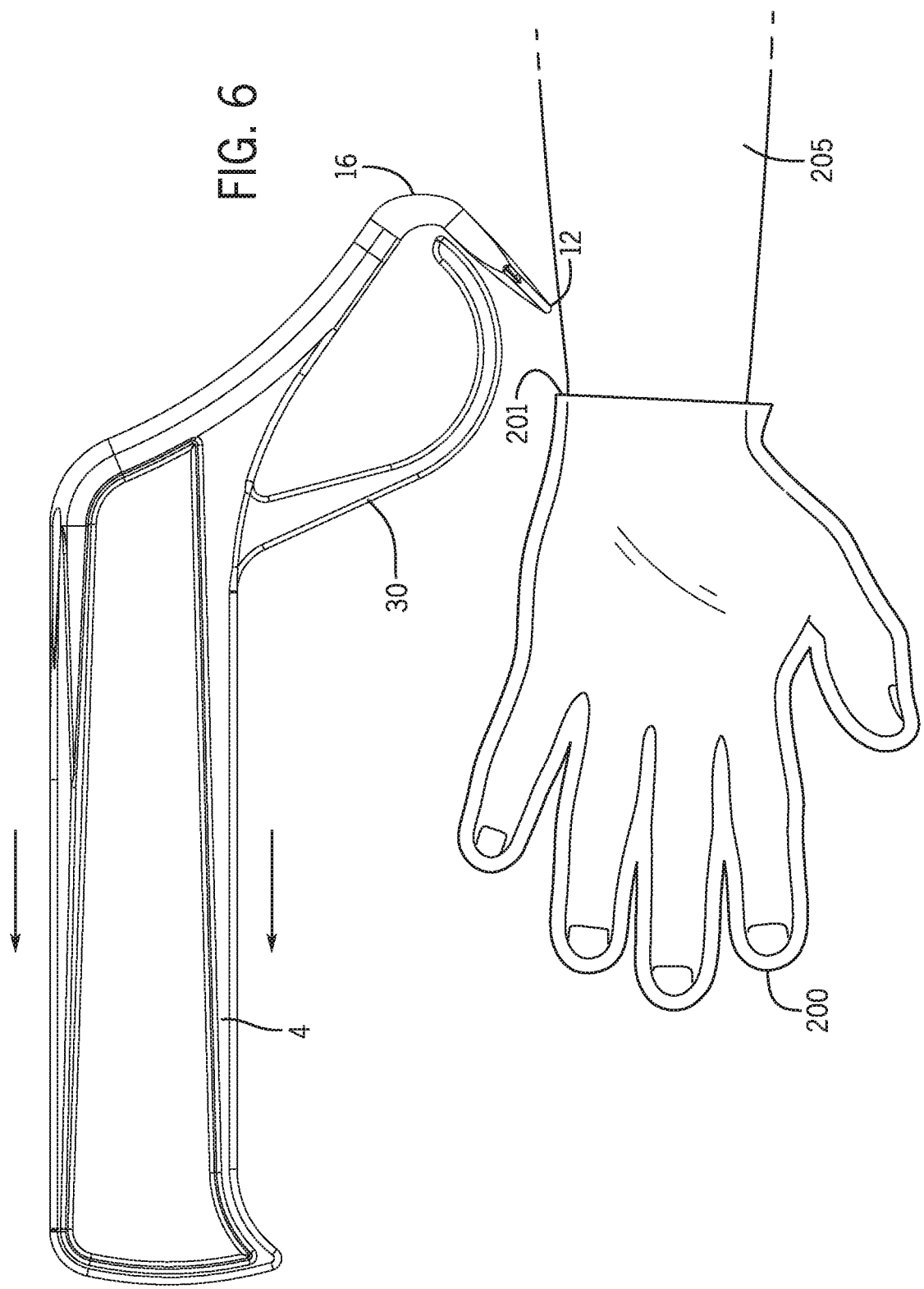
FIG. 6 illustrates the side view of the glove remover apparatus just prior to the apparatus sliding between the hand of a person and the glove in one embodiment.

The glove remover 1 is especially suitable for removing a glove 200 (FIGS. 6 and 7) from the hand/arm 205 of a person in a sterile manner. In an embodiment, the first end 2 of the apparatus 1 may have, for example, a prong 10. The prong 10 may be stationary with respect to the shaft 4. In an embodiment, the prong 10 may have a curved top surface 15 which terminates at a bend 16 at the first end 2 of the apparatus 1. The bend 16 may contact a contact surface 17 having a flat portion as best illustrated in FIG. 2.

Figure 4:
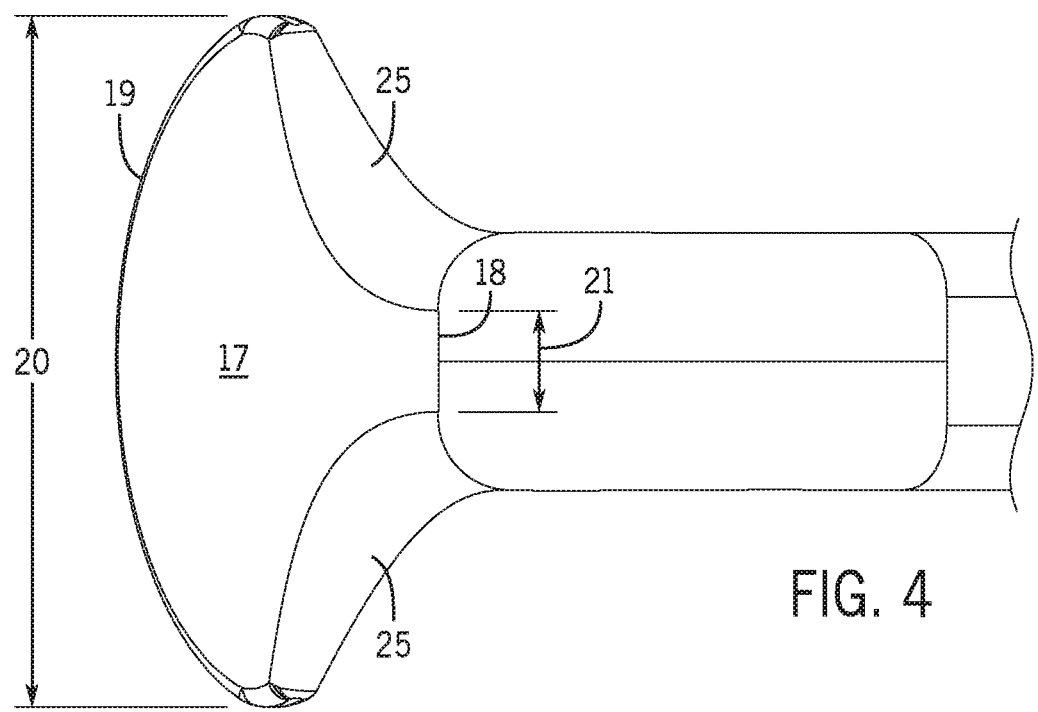
FIG. 4 illustrates a close up view of the generally flat portion of the glove remover apparatus in one embodiment.

In one embodiment, the contact surface 17 may have a first end 18 and a second end 19 wherein the second end 19 is generally curved and has a greater width 20 (FIG. 4) than a width 21 of the first end 18. The contact surface 17 may further have curved sides 25 so that the device 1 is less likely to rip a glove 200 or injure a person during use removing a glove 200. The curved second end 19 of the contact surface 17 may also allow the apparatus 1 to more easily and safely grasp the glove 200.

In an embodiment, a spring loaded trigger 30 (or "grasping mechanism") may contact the underside 31 of the contact surface 17. More specifically, the spring loaded trigger 30 may have a first end 40 and a second end 41 wherein the first end 40 of the spring loaded trigger 30 is permanently connected to the generally flat shaft 4 while the second end 41 of the spring loaded trigger 30 may move with respect to the first end 40 and the shaft 4. In the resting state, as shown in FIG. 1, the second end 41 of the spring loaded trigger 30 is forced against an underside 31 of the contact surface 17. In an embodiment, the second end 41 of the spring loaded trigger 30 always remains within the prong 10 portion of the apparatus 1 such that the contact surface 17 is always more distal than the second end 41 of the spring loaded trigger 30 with respect to the shaft 4.

When a light force is applied to a main body (or middle section) 44 of the spring loaded trigger 30, the force overcomes the spring loaded tension of the trigger 30 and forces the second end 41 of the spring loaded trigger 30 to slightly separate from underside 31 of the generally flat contact surface 17 of the apparatus 1. The force applied to the spring loaded trigger 30 may be, for example, created directly by a person's hand or may be created from the force of the glove 200 sliding between the second end 41 of the spring loaded trigger 30 and the underside 31 of the contact surface 17 as a person slides the apparatus 1 down the arm of the person and catches the glove 200 (as further described below).

Figure 7:
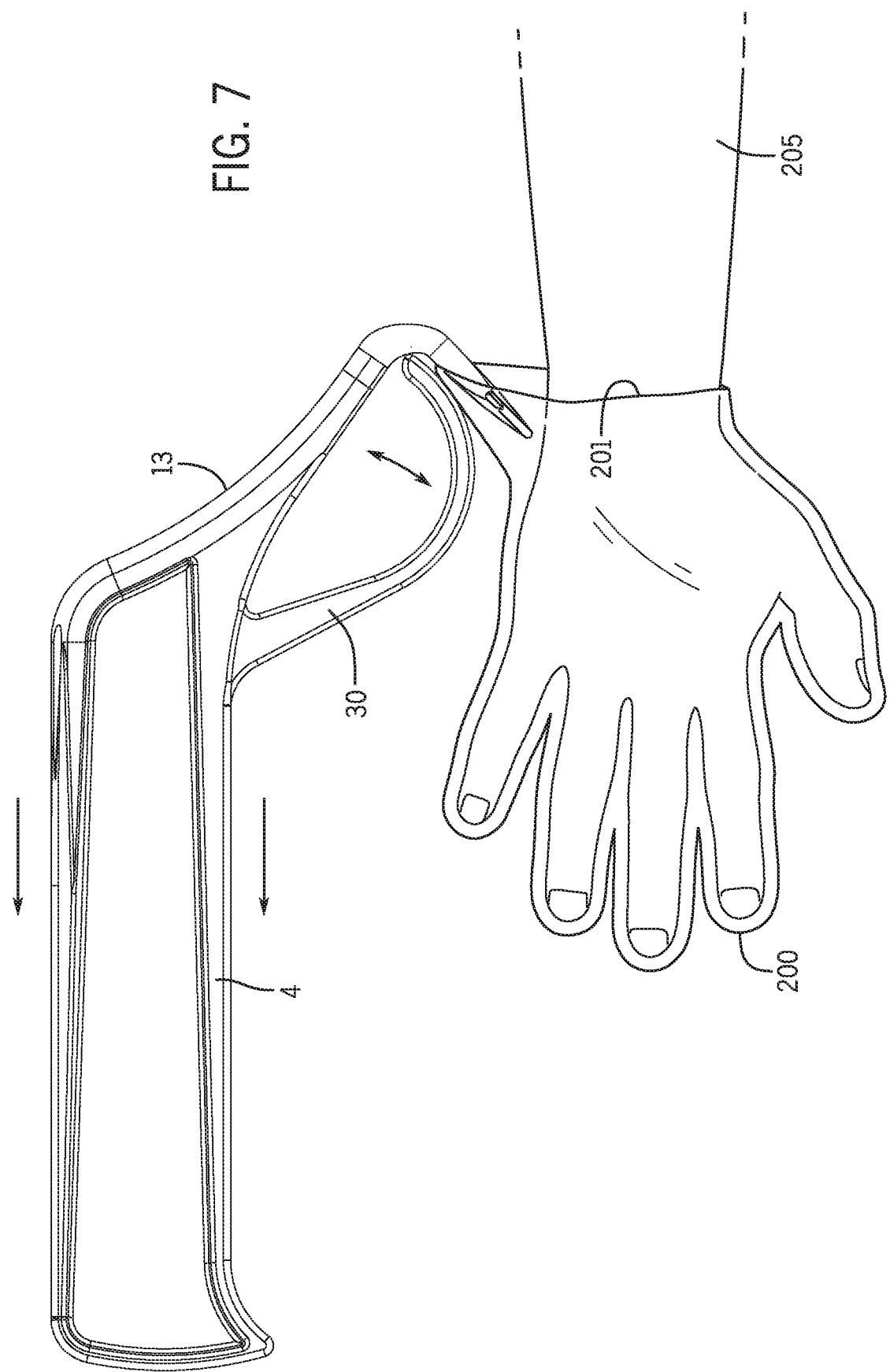
FIG. 7 illustrates the side view of the glove remover apparatus after the generally flat surface of the glove remover apparatus is located between the person's hand and the glove and wherein the spring trigger and generally flat surface of the glove remover apparatus has grasped and secured the glove.

As stated above, as the underside 31 of the contact surface 17 of the apparatus 1 slides along a person's arm 205, the underside 31 of the generally flat surface 17 slides between the open end 201 of the glove 200 and the person's arm 205. The lip of the open end 201 of the glove 200 and a portion of the glove 200 therein gets trapped (by friction) between the underside 31 of the contact surface 17 and the second end 41 of the spring loaded trigger 30 (as shown in FIG. 7).

Spring tension created by the spring loaded trigger 30 and the contact surface 17 of the prong 10 therein grasps at least the lip of the opening end 201 of the glove 200 and traps or 'locks' the glove 200 to the apparatus 1. A user then pulls the apparatus 1 (using his/her opposing or free hand) so that the apparatus 1 pulls off the glove 200 from his/her hand 205 while the glove 200 remains secured to the apparatus 1. As a result, the user is able to completely remove the glove 200 from his/her hand 205 without directly touching the used glove 200. This results in a sterile removal of the glove 200 from the hand 205, as is desired in an operation setting. The process may then be repeated (and reversed) to remove the remaining glove 200 from the other hand.

Figure 8:
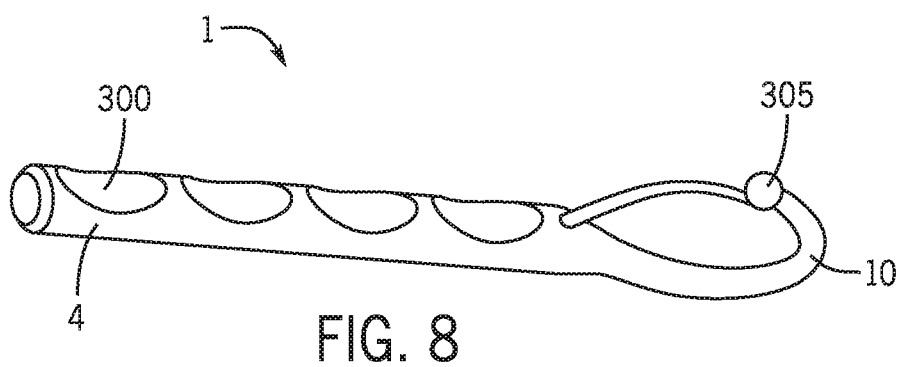
FIG. 8 illustrates an alternative embodiment of the glove apparatus remover apparatus wherein a ball is used at the distal end of the apparatus and wherein the handle is cylindrical, having finger grooves.
Figure 9:
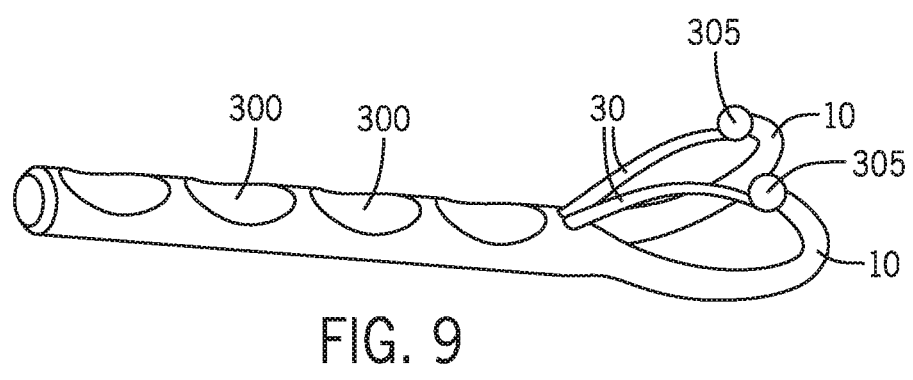
FIG. 9 illustrates another alternative embodiment of the glove remover apparatus wherein the apparatus has two prongs to remove a glove.

Referring now to FIG. 8, in an alternative embodiment, the apparatus 1 may use a ball 305 at the terminal end of the prong 10 as opposed to the generally flat contact surface 17 of the embodiment of FIG. 1. The ball 305 may be smooth to reduce ripping of the glove 200 or injuring the arm 205 of a person. Further, in an alternative embodiment, the shaft 4 portion may be cylindrical and may have, for example, finger grooves 300 for easy grasping of the apparatus 1. Still further, in an embodiment (not shown) the generally flat shaft 4 of FIG. 1 may also have finger grooves 300 similar to the grooves of FIGS. 8 and 9. Referring now to FIG. 9, in one alternative embodiment, two prongs 10 are used to grasp the glove 200 at the same time.

Because the generally smooth spherical balls 305 of FIGS. 8 and 9 are the only part of the apparatus 1 to make physical contact with the skin of the user, the smooth spherical balls 305 therein prevent scratching or injury to the person. In one embodiment (not shown) the apparatus 1 may have more or less prongs than the two illustrated in FIG. 8 or 9.

Although embodiments of the invention are shown and described therein, it should be understood that various changes and modifications to the presently preferred embodiments will be apparent to those skilled in the art. Such changes and modifications may be made without departing from the spirit and scope of the invention and without diminishing its attendant advantages.

We claim:

1. A glove remover apparatus comprising:
a shaft extending along a straight axis wherein the shaft has a first end and a second end;
a prong having a main unit and a contact surface wherein the prong extends downward and away from the first end of the shaft at an angle and in a non-parallel manner with respect to the straight axis of the shaft;
wherein the contact surface of the prong extends in a perpendicular manner with respect to the main unit;
a spring loaded trigger which moves from a first position to a second position and wherein in the first position the spring loaded trigger rests on the contact surface of the prong and wherein in the second position the spring loaded trigger grasps a glove and secures the glove between the contact surface and the trigger;
wherein the glove remover apparatus is made of plastic and infused with an antibacterial agent;
wherein the contact surface has a first end and a second end and wherein the second end of the contact surface has a greater width than a width of the first end of the contact surface; and
wherein the contact surface has a greater width than a width of the spring loaded trigger.

2. The glove remover apparatus of claim 1 wherein the grasping mechanism secures the glove by friction.

3. The glove remover apparatus of claim 1 wherein the distal end of the contact surface is curved.

4. The glove remover apparatus of claim 1 wherein the distal end of the grasping mechanism lacks a sharp point.

5. The glove remover apparatus of claim 1 further comprising:
   at least one finger groove on the shaft for grasping the shaft.

6. The glove remover apparatus of claim 1 wherein the second end of the contact surface is curved.

\* \* \* \* \*